United States Patent
Chen et al.

(10) Patent No.: US 7,119,109 B2
(45) Date of Patent: Oct. 10, 2006

(54) HETEROARYLHETEROALKYLAMINE DERIVATIVES AND THEIR USE AS INHIBITORS OF NITRIC OXIDE SYNTHASE

(75) Inventors: Deborah Chen, Wilmington, DE (US); David Cheshire, Loughborough (GB); Stephen Connolly, Loughborough (GB); Antonio Mete, Loughborough (GB)

(73) Assignee: Astrazeneca AB, Sodertalje (SE)

( * ) Notice: Subject to any disclaimer, the term of this patent is extended or adjusted under 35 U.S.C. 154(b) by 233 days.

(21) Appl. No.: 10/484,960

(22) PCT Filed: Jul. 26, 2002

(86) PCT No.: PCT/SE02/01415

§ 371 (c)(1),
(2), (4) Date: Jan. 27, 2004

(87) PCT Pub. No.: WO03/011831

PCT Pub. Date: Feb. 13, 2003

(65) Prior Publication Data

US 2004/0220234 A1 Nov. 4, 2004

(30) Foreign Application Priority Data

Jul. 31, 2001 (SE) .................... 0102639

(51) Int. Cl.
*A61K 31/44* (2006.01)
*C07D 211/78* (2006.01)

(52) U.S. Cl. ..................... 514/344; 546/288
(58) Field of Classification Search ............... 546/288; 514/344

See application file for complete search history.

(56) References Cited

U.S. PATENT DOCUMENTS 3,535,328 A * 10/1970 Zielinski ................... 546/268.1
4,666,910 A    5/1987 Schneider et al.
2004/0176422 A1 * 9/2004 Birkinshaw et al. ........ 514/344

FOREIGN PATENT DOCUMENTS

EP  0399504 A2  11/1990
EP  0571685 A1  12/1993
EP  0707007 A1  4/1996
GB  2060622 A   5/1981

OTHER PUBLICATIONS

Exp. Opin. Ther. Patents (2000) 10 (1) :125-129.*
Guslandi, M. "Nitric Oxide and inflammatory bowel diseases", European Journal of Clinical Investigation (1998), 28, 904-907.*
Hcaplus 134:40195.*
Hcaplus 137:346227.*
Hcaplus 131:97231.*
Hcaplus 135:147512.*
STN International, file Caplus, Caplus accession No. 1977:189458, document No. 86:189458, Rohto Pharmaceuticals Co., Ltd.: "Aromatic amino ether quaternary ammonium salts"; JP, B4, 51044934; 19761201.

* cited by examiner

*Primary Examiner*—Cecilia J. Teang
*Assistant Examiner*—Binta Robinson
(74) *Attorney, Agent, or Firm*—White & Case LLP

(57) ABSTRACT

There are provided novel compounds of formula (I)

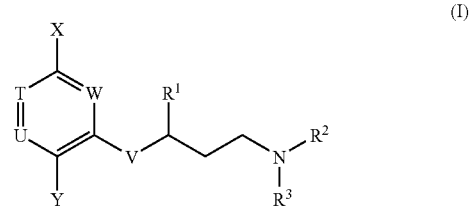

wherein $R^1$, $R^2$, $R^3$, T, U, X, Y, V and W are as defined in the specification, and pharmaceutically acceptable salts thereof; together with processes for their preparation, compositions containing them and their use in therapy. The compounds are inhibitors of nitric oxide synthase and are thereby particularly useful in the treatment or prophylaxis of inflammatory disease, CNS disorders and pain.

15 Claims, No Drawings

HETEROARYLHETEROALKYLAMINE DERIVATIVES AND THEIR USE AS INHIBITORS OF NITRIC OXIDE SYNTHASE

FIELD OF THE INVENTION

The present invention relates to novel heteroarylheteroalkylamine derivatives, processes for their preparation, compositions containing them and their use in therapy.

BACKGROUND OF THE INVENTION

Nitric oxide is produced in mammalian cells from L-arginine by the action of specific nitric oxide synthases (NOSs). These enzymes fall into two distinct classes—constitutive NOS (cNOS) and inducible NOS (iNOS). At the present time, two constitutive NOSs and one inducible NOS have been identified. Of the constitutive NOSs, an endothelial enzyme (eNOS) is involved with smooth muscle relaxation and the regulation of blood pressure and blood flow, whereas the neuronal enzyme. (nNOS) appears to be involved in the regulation of various biological functions. Inducible NOS has been particularly implicated in the pathogenesis of inflammatory diseases. Regulation of these enzymes should therefore offer considerable potential in the treatment of a wide variety of disease states (J. E. Macdonald, *Ann. Rep. Mea Chem.*, 1996, 31, 221–230).

Considerable effort has been expended to identify compounds that act as specific inhibitors of one or more isoforms of the enzyme nitric oxide synthase. The use of such compounds in therapy has also been widely claimed.

DISCLOSURE OF THE INVENTION

According to the present invention, there is provided a compound of formula (I)

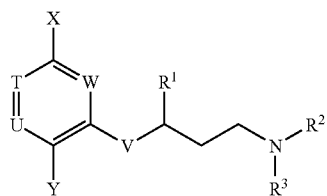

(I)

wherein
X represents H, C1 to 4 alkyl, C1 to 4 alkoxy, halogen, OH, CN, C≡CH, $NO_2$, CHO, $COCH_3$ or NHCHO; said alkyl or alkoxy group being optionally further substituted by one or more fluorine atoms or by an OH group;
Y represents C1 to 4 alkyl, C1 to 4 alkoxy, halogen, OH, CN, C≡CH, $NO_2$, CHO, $COCH_3$ or NHCHO; said alkyl or alkoxy group being optionally further substituted by one or more fluorine atoms;
One of T, U and W represents N and the other two independently represent CR; and each $R^4$ group independently represents H, F or $CH_3$;
V represents O or $S(O)_n$;
n represents an integer 0, 1 or 2;
$R^1$ represents C1 to 4 alkyl, C2 to 4 alkenyl, C2 to 4 alkynyl, C3 to 6 cycloalkyl or a 4 to 8 membered saturated heterocyclic ring incorporating one heteroatom selected from O, S and N; any of said groups being optionally farther substituted by C1 to 4 alkyl, C1 to 4 alkoxy, C1 to 4 alkylthio, C3 to 6 cycloalkyl, one or more halogens or phenyl; said phenyl group being optionally further substituted by one or more substituents selected independently from halogen, C1 to 4 alkyl, C1 to 4 alkoxy, $CF_3$, $OCF_3$, CN or $NO_2$;
$R^2$ and $R^3$ independently represent H, C1 to 4 alkyl or C3 to 6 cycloalkyl; said alkyl group being optionally substituted by C1 to 4 alkoxy, halogen, hydroxy, -Z-$NR^7R^8$, phenyl or a five or six membered aromatic or saturated heterocyclic ring containing 1 to 3 heteroatoms independently selected from O, S and N; said phenyl or aromatic heterocyclic ring being optionally further substituted by halogen, C1 to 4 alkyl, C1 to 4 alkoxy, $CF_3$, $OCF_3$, CN or $NO_2$;
Z represents —CO— or a bond;
$R^7$ and $R^8$ independently represent H or C1 to 4 alkyl;
or a pharmaceutically acceptable salt thereof It will be recognised that compounds of formula (I) wherein W represents N and X represents OH may exist in the alternative tautomeric form (Ia):

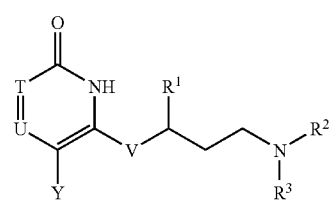

(Ia)

Analogous tautomeric structures will also exist for compounds of formula (I) wherein T represents N and X represents OH; or wherein U represents N and Y represents OH. All such tautomeric forms and mixtures thereof are included within the scope of the invention.

The compounds of formula I may exist in enantiomeric forms. Therefore, all enantiomers, diastereomers, racemates and mixtures thereof are included within the scope of the invention.

The compounds of formula (I) and their pharmaceutically acceptable salts have the advantage that they are inhibitors of the enzyme nitric oxide synthase (NOS). In general, the compounds of formula (I) and their pharmaceutically acceptable salts have the advantage that they are inhibitors of the inducible isoform of the enzyme nitric oxide synthase (iNOS). Certain compounds of formula (I) and their pharmaceutically acceptable salts have the advantage that they are additionally or alternatively inhibitors of the neuronal isoform of the enzyme nitric oxide synthase (nNOS). In general, compounds of formula (I) and their pharmaceutically acceptable salts have the advantage that they show good selectivity for the inhibition of iNOS and/or nNOS in comparison to the inhibition of the endothelial isoform, eNOS.

The invention further provides a process for the preparation of compounds of formula (I) or a pharmaceutically acceptable salt, enantiomer or racemate thereof.

According to the invention there is also provided a compound of formula (I), or a pharmaceutically acceptable salt thereof, for use as a medicament.

Another aspect of the invention provides the use of a compound of formula (I) or a pharmaceutically acceptable salt thereof in the manufacture of a medicament, for the treatment or prophylaxis of diseases or conditions in which inhibition of nitric oxide synthase activity is beneficial.

Another aspect of the invention provides the use of a compound of formula (I) or a pharmaceutically acceptable salt thereof, in the manufacture of a medicament, for the treatment or prophylaxis of diseases or conditions in which inhibition of iNOS activity is beneficial.

Another aspect of the invention provides the use of a compound of formula (I) or a pharmaceutically acceptable salt thereof in the manufacture of a medicament, for the treatment or prophylaxis of diseases or conditions in which inhibition of nNOS activity is beneficial.

Another aspect of the invention provides the use of a compound of formula (I) or a pharmaceutically acceptable salt thereof, in the manufacture of a medicament, for the treatment or prophylaxis of inflammatory disease.

Another aspect of the invention provides the use of a compound of formula (I) or a pharmaceutically acceptable salt thereof; in the manufacture of a medicament, for the treatment or prophylaxis of CNS disease.

According to the invention, there is also provided a method of treating, or reducing the risk of, diseases or conditions in which inhibition of nitric oxide synthase activity is beneficial which comprises administering to a person suffering from or at risk of; said disease or condition, a therapeutically effective amount of a compound of formula (I) or a pharmaceutically acceptable salt thereof.

There is also provided a method of treating, or reducing the risk of, inflammatory disease in a person suffering from or at risk of, said disease, wherein the method comprises administering to the person a therapeutically effective amount of a compound of formula (I) or a pharmaceutically acceptable salt thereof.

There is also provided a method of treating, or reducing the risk of CNS disease in a person suffering from or at risk of, said disease, wherein the method comprises administering to the person a therapeutically effective amount of a compound of formula (I) or a pharmaceutically acceptable salt thereof.

The compounds of the present invention may also be used advantageously in combination with a second pharmaceutically active substance; particularly in combination with a cyclooxygenase inhibitor; more particularly in combination with a selective inhibitor of the inducible isoform of cyclooxygenase (COX-2). Thus, in a further aspect of the invention there is provided the use of a compound of formula (I) or a pharmaceutically acceptable salt thereof, in combination with a COX-2 inhibitor in the manufacture of a medicament for the treatment of inflammation, inflammatory disease and inflammatory related disorders. And there is also provided a method of treating, or reducing the risk of, inflammation, inflammatory disease and inflammatory related disorders in a person suffering from or at risk of; said disease or condition, wherein the method comprises administering to the person a therapeutically effective amount of a compound of formula (I) or a pharmaceutically acceptable salt thereof in combination with a COX-2 inhibitor.

In one embodiment, V represents $S(O)_n$ and n represents 0.

In another embodiment, V represents O.

In another embodiment, X and Y independently represent Br, Cl, $CH_3$, $CH_3CH_2$, $CH_2F$, $CHF_2$, $CF_3$, $NO_2$ or CN.

In one embodiment, X represents $CH_3$, $CH_3CH_2$ or $CF_3$.

In another embodiment Y represents CN.

In one embodiment, $R^2$ represents H or $CH_3$.

In one embodiment, $R^3$ represents H or $CH_3$.

In one embodiment, each $R^4$ represents H or F.

In another embodiment, one of the groups T, U and W represents N, and the other two groups independently represent CH or CF. In a particular embodiment, W represents N, T represents CH or CF and U represents CH.

In a particular embodiment, the compounds of formula (I) have the absolute stereochemistry as shown in formula (Ib):

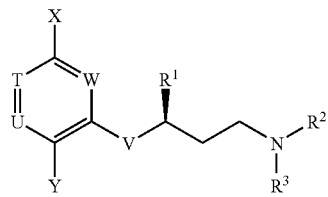

(Ib)

In one particular aspect the invention relates to compounds of formula (I) wherein V represents O or S; X and Y independently represent Br, Cl, $CH_3$, $CH_3CH_2$, $CH_2F$, $CHF_2$, $CF_3$, $NO_2$ or CN; $R^2$ and $R^3$ independently represent H or $CH_3$; $R^4$ represents H or F; one of the groups T, U and W represents N, and the other two groups independently represent CH or CF; and pharmaceutically acceptable salts thereof.

Particular compounds of the invention include:
6-methyl-2-{3-[1-methylaminohexyl]thio}nicotinonitrile;
6-trifluoromethyl-2-{3-[1-methylaminohexyl]thio}nicotinonitrile;
2-[1-ethyl-3-(methylamino)propoxy]-6-(trifluoromethyl)-3-pyridinecarbonitrile;
2-[[1-ethyl-3-(methylamino)propyl]thio]-6-methyl-3-pyridinecarbonitrile;
2-[1-cyclopentyl-3-(methylamino)thiopropyl]-6-(trifluoromethyl)-3-pyridinecarbonitrile;
2-[1-cyclopentyl-3-(methylamino)thiopropyl]-6-methyl-3-pyridinecarbonitrile;
(R)-2-(3-methylamino-1-trifuoromethylpropoxy)-6-trifluoromethyl-nicotinonitrile;
(R)-5-fluoro-6-methyl-2-(3-methylamino-1-trifluoromethylpropoxy)nicotinonitrile;
(R)-6-ethyl-5-fluoro-2-(3-methylamino-1-trifluoromethylpropoxy)nicotinonitrile;
6-methyl-2-(3-methylamino-1-trifluoromethylpropoxy)nicotinonitrile;
2-(3-amino-1-trifluoromethylpropoxy)-6-trifluoromethylnicotinonitrile;
5-fluoro-6-ethyl-2-{3-[1-methylaminopentyl]thio}nicotinonitrile;
6-trifluoromethyl-2-{3-[1-methylaminopentyl]thio}nicotinonitrile;
6-methyl-2-{3-[1-methylaminohex-5-enyl]thio}nicotinonitrile;
2-[1-(2-aminoethyl)-2,2 3,3,3-pentafluoropropoxy]-6-trifluoromethyl-nicotinonitrile;
2-[1-(2-aminoethyl)-2,2,3,3,3-pentafluoropropoxy]-6-methyl-nicotinonitrile;
and pharmaceutically acceptable salts thereof.

Unless otherwise indicated, the term "C1 to 4 alkyl" referred to herein denotes a straight or branched chain alkyl group having from 1 to 4 carbon atoms. Examples of such groups include methyl, ethyl, n-propyl, i-propyl, n-butyl, i-butyl and t-butyl.

Unless otherwise indicated, the term "C3 to 6 cycloalkyl" referred to herein denotes a cycloalkyl group having from 3 to 6 carbon atoms. Examples of such groups include cyclopropyl, cyclopentyl and cyclohexyl.

Unless otherwise indicated, the term "C2 to 4 alkenyl" referred to herein denotes a straight or branched chain alkyl group having from 2 to 4 carbon atoms incorporating at least one carbon-carbon double bond. Examples of such groups include ethenyl, propenyl and butenyl.

Unless otherwise indicated, the term "C2 to 4 alkynyl" referred to herein denotes a straight or branched chain all group having from 2 to 4 carbon atoms incorporating at least one carbon-carbon triple bond. Examples of such groups include ethynyl, propynyl, and butenyl.

Unless otherwise indicated, the term "C1 to 4 alkoxy" referred to herein denotes a straight or branched chain alkoxy group having from 1 to 4 carbon atoms. Examples of such groups include methoxy, ethoxy, n-propoxy, i-propoxy and t-butoxy.

The term "C1 to 4 alkylthio" is to be interpreted analogously.

Unless otherwise indicated, the term "halogen" referred to herein denotes fluoro, chloro, bromo and iodo.

Examples of a 4 to 8 membered saturated heterocyclic ring incorporating one heteroatom selected from O, S or N include pyrrolidine, piperidine, tetrahydrofuran and perhydroazepine.

Examples of a five or six membered aromatic heterocyclic ring containing 1 to 3 heteroatoms independently selected from O, S and N include furan, thiophene, pyridine, thiazole, imidazole, oxazole, triazole, oxadiazole, thiadiazole and pyrimidine.

Examples of a five or six membered saturated heterocyclic ring containing 1 to 3 heteroatoms independently selected from O, S and N include morpholine, pyrrolidine, tetrahydrofuran, piperidine and piperazine.

Examples of a "C1 to 4 alkyl or C1 to 4 alkoxy optionally further substituted by one or more fluorine atoms" include $CH_2F$, $CHF_2$, $CF_3CF_3CF_2$, $CF_3CH_2$, $CH_2FCH_2$, $CH_3CF_2$, $CF_3CH_2CH_2$, $OCF_3$ and $OCH_2CF_3$.

According to the invention, we further provide a process for the preparation of compounds of formula (I), or a pharmaceutically acceptable salt, enantiomer or racemate thereof which comprises:

(a) reaction of a compound of formula (II)

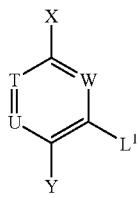

(II)

wherein T, U, X, Y and W are as defined in formula (I) and $L^1$ represents a leaving group, with a compound of formula (III)

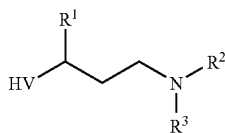

(III)

wherein $R^1$, $R^2$, $R^3$ and V are as defined in formula (I); or (b) reaction of a compound of formula (IV)

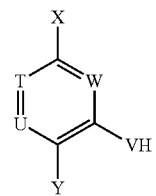

(IV)

wherein T, U, W, X, Y and V are as defined in formula (I), with a compound of formula (V)

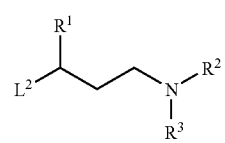

(V)

wherein $R^1$, $R^2$ and $R^3$ are as defined in formula (I) and $L^2$ is a leaving group; or (c) reaction of a compound of formula (VI)

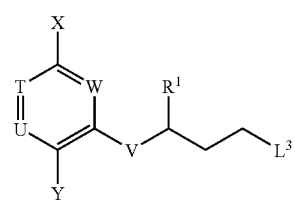

(VI)

wherein $R^1$, T, U, W, X, Y and V are as defined in formula (I) and $L^3$ is a leaving group, with a compound of formula (VII)

$R^2R^3NH$ (VII)

wherein $R^2$ and $R^3$ are as defined in formula (I); or (d) reduction of a compound of formula (VIII)

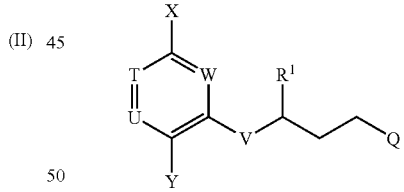

(VIII)

wherein $R^1$, T, U, W, X, Y and V are as defined in formula (I) and Q represents azide ($N_3$); or (e) hydrolysis of a compound of formula (VIII)

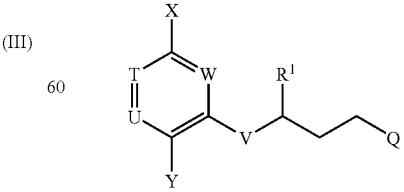

(VIII)

wherein $R^1$, T, U, W, X, Y and V are as defined in formula (I) and Q represents an imide group;

and where desired or necessary converting the resultant compound of formula (I), or another salt thereof, into a pharmaceutically acceptable salt thereof or converting one compound of formula (I) into another compound of formula (I); and where desired converting the resultant compound, of formula (I) into an optical isomer thereof.

In process (a), the reaction is performed by treating a nucleophile of formula (III) with an electrophile of formula (II) in an inert solvent. Suitable leaving groups $L^1$ include sulphonates and halides, particularly fluoride or chloride. The reaction is generally performed in the presence of a non-nucleophilic base such as sodium hydride or caesium carbonate. Suitable organic solvents are those such as N,N-dimethylformamide, N-methyl-2-pyrrolidinone, tetrahydrofuran and dimethylsulfoxide. The reaction is generally conducted at a temperature between 0° C. and the boiling point of the solvent.

In process (b), the reactants (IV) and (V) are coupled together in a suitable inert solvent such as tetrahydrofuran using, for example, Mitsunobu conditions. Thus, for example, the reactants are treated with a phosphine derivative and an azo derivative at a suitable temperature, generally between 0° C. and the boiling point of the solvent. Suitable phosphine derivatives include triphenylphosphine and tributylphosphine. Suitable azo derivatives include diethyl azodicarboxylate, diisopropyl azodicarboxylate and 1,1'-(azodicarbonyl)dipiperidine. Suitable leaving groups $L^2$ include hydroxy.

Alternatively in process (b), the reaction is performed by treating a nucleophile of formula (IV) with an electrophile of formula (V) in an inert solvent. Suitable leaving groups $L^2$ include sulphonates and halides, particularly chloride or bromide. The reaction is generally performed in the presence of a non-nucleophilic base such as sodium hydride or caesium carbonate. Suitable organic solvents are those such as N,N-dimethylformamide, N-methyl-2-pyrrolidinone, tetrahydrofuran and dimnethylsulfoxide. The reaction is generally conducted at a temperature between 0° C. and the boiling point of the solvent.

In process (c), the compounds of formulae (VI) and (VII) are reacted together in a suitable inert-solvent such as dimethylsulphoxide or tetrahydrofuran. The reaction is generally carried out in the presence of a base. The base may be either an added component or an excess of the amine (VII). Suitable leaving groups $L^3$ include iodide and p-toluenesulphonate.

In processes (d) and (e), the reactions are carried out using standard conditions that will be well known to the man skilled in the art.

It will be apparent to a person skilled in the art that in the above processes it may be desirable or necessary to protect an amine or hydroxyl or other potentially reactive group. Suitable protecting groups and details of processes for adding and removing such groups may be found by reference to the standard text "Protective Groups in Organic Synthesis", 3rd Edition (1999) by Greene and Wuts.

In one preferred embodiment, amine groups are protected as carbamate derivatives, for example, as t-butyloxycarbamates.

Specific examples of the use of protecting groups are given in the Examples section The present invention includes compounds of formula (I) in the form of salts, in particular acid addition salts. Suitable salts include those formed with both organic and inorganic acids. Such acid addition salts will normally be pharmaceutically acceptable although salts of non-pharmaceutically acceptable acids may be of utility in the preparation and purification of the compound in question. Thus, preferred salts include those formed from hydrochloric, hydrobromic, sulphuric, phosphoric, citric, tataric, lactic, pyruvic, acetic, succinic, fumaric, maleic, methanesulphonic and benzenesulphonic acids.

Salts of compounds of formula (I) may be formed by reacting the free base, or a salt, enantiomer or racemate thereof with one or more equivalents of the appropriate acid. The reaction may be carried out in a solvent or medium in which the salt is insoluble or in a solvent in which the salt is soluble, for example, water, dioxane, ethanol, tetrahydrofuran or diethyl ether, or a mixture of solvents, which may be removed in vacuo or by freeze drying. The reaction may also be a metathetical process or it may be carried out on an ion exchange resin.

Compounds of formula (III) may be prepared by reaction of a compound of formula (IX)

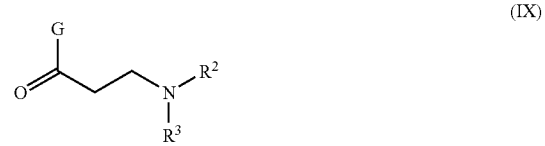

wherein $R^2$ and $R^3$ are as defined in formula (I), and G represents H, Cl or $NCH_3(OCH_3)$, with an organometallic derivative, $R^1$-M, wherein $R^1$ is as defined in formula (I) and M represents a metallic residue such as lithium or magnesium-halide, followed if necessary by reduction. The resulting compound of formula (III) wherein V represents oxygen may then be subsequently converted into compounds of formula (III) wherein V represents sulphur.

Compounds of formulae (II), (IV), (V), (VI), (VIII) and (IX) are either known or may be prepared by conventional methods that will be readily apparent to the man skilled in the art.

Intermediate compounds may be used as such or in protected form. Protecting groups and details of processes for their removal may be found by reference to the standard text "Protective Groups in Organic Synthesis", 3rd Edition (1999) by Greene and Wuts.

The compounds of the invention and intermediates thereto may be isolated from their reaction mixtures and, if necessary further purified, by using standard techniques.

The compounds of formula I may exist in enantiomeric forms. Therefore, all enantiomers, diastereomers, racemates and mixtures thereof are included within the scope of the invention. The various optical isomers may be isolated by separation of a racemic mixture of the compounds using conventional techniques, for example, fractional crystallisation, or HPLC.

Intermediate compounds may also exist in enantiomeric forms and may be used as purified enantiomers, diastereomers, racemates or mixtures.

The compounds of formula (I), and their pharmaceutically acceptable salts, are useful because they possess pharmacological activity in animals. In particular, the compounds are active as inhibitors of the enzyme nitric oxide synthase. More particularly, they are inhibitors of the inducible isoform of the enzyme nitric oxide synthase and as such are predicted to be useful in therapy, for example, as anti-inflammatory agents. Alternatively or additionally, they may have utility as inhibitors of the neuronal isoform of the enzyme nitric oxide synthase and as such are predicted to have utility in the treatment of CNS disorders.

The compounds and their pharmaceutically acceptable salts are indicated for use in the treatment or prophylaxis of diseases or conditions in which synthesis or oversynthesis of nitric oxide forms a contributory part. In one aspect, the compounds are indicated for use in the treatment of inflammatory conditions m mammals including man. In another aspect, the compounds are indicated for use in the treatment of CNS disorders in mammals including man.

As used herein, reference to any of the terms "disease", "condition" and "disorder" is to be taken as a reference to all three terms.

Diseases, conditions and disorders that may be specifically mentioned are:

osteoarthritis, rheumatoid arthritis, rheumatoid spondylitis, gouty arthritis and other arthritic conditions, inflamed joints;

eczema, psoriasis, dermatitis or other inflammatory shin conditions such as sunburn;

inflammatory eye conditions including uveitis, glaucoma and conjunctivitis;

lung disorders in which inflammation is involved, for example, asthma, bronchitis, chronic obstructive pulmonary disease, pigeon fancier's disease, farmer's lung, acute respiratory distress syndrome;

bacteraemia, endotoxaemia (septic shock), aphthous ulcers, gingivitis, pyresis, pain, meningitis and pancreatitis;

conditions of the gastrointestinal tract including inflammatory bowel disease, Crohn's disease, atrophic gastritis, gastritis varialoforme, ulcerative colitis, coeliac disease, regional ileitis, peptic ulceration, irritable bowel syndrome, reflux oesophagitis, damage to the gastrointestinal tract resulting from infections by, for example, *Helicobacter pylori*, or from treatments with non-steroidal anti-inflammatory drugs;

and other conditions associated with inflammation.

The compounds may also be useful in the treatment of cancer.

The compounds may also be useful in the treatment and alleviation of acute pain or persistent inflammatory pain or neuropathic pain or pain of a central origin.

We are particularly interested in the conditions inflammatory bowel disease, rheumatoid arthritis, osteoarthritis, chronic obstructive pulmonary disease, pain and cancer.

The compounds of formula (I) and their pharmaceutically acceptable salts may also be useful in the treatment or prophylaxis of diseases or conditions in addition to those mentioned above. For example, the compounds may be useful in the treatment of atherosclerosis, cystic fibrosis, hypotension associated with septic and/or toxic shock, in the treatment of dysfunction of the immune system, as an adjuvant to short-term immunosuppression in organ transplant therapy, in the control of onset of diabetes, in the maintenance of pancreatic function in diabetes, in the treatment of vascular complications associated with diabetes and in co-therapy with cytokines, for example TNF or interleukins.

The compounds of formula (I) may also be useful in the treatment of hypoxia, for example in cases of cardiac arrest and stroke, neurodegenerative disorders including nerve degeneration and/or nerve necrosis in disorders such as ischaemia, hypoxia, hypoglycaemia, epilepsy, and in external wounds (such as spinal cord and head injury), hyperbaric oxygen convulsions and toxicity, dementia, for example pre-senile dementia, Alzheimer's disease and AIDS-related dementia, Syderham's chorea, Parkinson's disease, Tourette's Syndrome, Huntington's disease, Amyotrophic Lateral Sclerosis, Multiple Sclerosis, muscular dystrophy, Korsakoff's disease, imbecility relating to a cerebral vessel disorder, sleeping disorders, schizophrenia, depression, pain, autism, seasonal affective disorder, jet-lag, depression or other symptoms associated with Premenstral Syndrome (PMS), anxiety and septic shock. Compounds of formula (I) may also be expected to show activity in the prevention and reversal of drug addiction or tolerance such as tolerance to opiates and diazepines, treatment of drug addiction, treatment of migraine and other vascular headaches, neurogenic inflammation, in the treatment of gastrointesial motility disorders and in the induction of labour.

We are particularly interested in the conditions stroke, Alzheimer's disease, Parkinson's disease, multiple sclerosis, schizophrenia, migraine, septic shock and pain; more particularly migraine.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

For the above mentioned therapeutic indications, the dosage administered will, of course, vary with the compound employed, the mode of administration and the treatment desired. However, in general, satisfactory results are obtained when the compounds are administered at a dosage of the solid form of between 1 mg and 2000 mg per day.

The compounds of formula (I), and pharmaceutically acceptable derivatives thereof, may be used on their own, or in the form of appropriate pharmaceutical compositions in which the compound or derivative is in admixture with a pharmaceutically acceptable adjuvant, diluent or carrier. Thus, another aspect of the invention provides a pharmaceutical composition comprising a compound of formula (I) or a pharmaceutically acceptable salt thereof, in admixture with a pharmaceutically acceptable adjuvant, diluent or carrier. Administration may be by, but is not limited to, enteral (including oral, sublingual or rectal), intranasal, inhalation, intravenous, topical or other parenteral routes. Conventional procedures for the selection and preparation of suitable pharmaceutical formulations are described in, for example, "Pharmaceuticals—The Science of Dosage Form Designs", M. E. Aulton, Churchill Livingstone, 1988. The pharmaceutical composition preferably comprises less than 80% and more preferably less than 50% of a compound of formula (I), or a pharmaceutically acceptable salt thereof.

There is also provided a process for the preparation of such a pharmaceutical composition which comprises mixing the ingredients.

The compounds of formula (I), and pharmaceutically acceptable derivatives thereof may also be advantageously used in combination with a COX inhibitor, more particularly in combination with a COX-2 inhibitor. Particularly preferred COX-2 inhibitors are Celecoxib and MK-966. The NOS inhibitor and the COX-2 inhibitor may either be formulated together within the same pharmaceutical composition for administration in a single dosage unit, or each component may be individually formulated such that separate dosages may be administered either simultaneously or sequentially.

The invention is illustrated, but in no way limited, by the following examples:

EXAMPLE 1

6-Methyl-2-{3-[1-methylaminohexyl]thio}nicotinonitrile dihydrochloride a) (3-Hydroxyhexyl)methylcarbamic acid, 1,1-dimethylethyl ester

To an ice-cooled stirred solution of methyl-(3-oxopropyl)carbamic acid, 1,1-dimethylethyl ester (11.0 g, 59 mmol) in dry tetrahydrofuran (120 ml) under nitrogen was added a 2M solution of n-propylmagnesium chloride in ether (36 ml). The resulting mixture was stirred at 0° C. for 30 minutes, then allowed to warm to room temperature with sting over 20 h, and quenched by dropwise addition of saturated aqueous ammonium chloride. The supernatant solution was decanted from the white solids and concentrated to dryness to give the title compound (11.5 g) as an oil.

$^1$H NMR 300 MHz (CDCl$_3$) 3.70 (1H, bs), 3.47 (1H, bs), 2.83 (3H, s), 1.63 (2H, m), 1.20–1.50 (15H, m), 0.90 (3H, t).

b) [3-(Acetylthio)-hexyl]methylcarbamic acid, 1,1-dimethylethyl ester

To an ice-cooled stirred solution of triphenylphosphine (25.0 g, 95.4 mmol) in tetrahydrofuran (450 ml) under nitrogen was added dropwise diisopropyl azodicarboxylate (19 ml, 93.3 mmol). After 0.5 h, a solution of (3-hydroxyhexyl)methylcarbamic acid, 1,1-dimethylethyl ester (11.5 g, 49.8 mmol) and thiolacetic acid (6.8 ml, 95.2 mmol) in tetrahydrofuran (50 ml) was added slowly. The resulting mixture was stirred at 0° C. for 1 h, then allowed to warm to room temperature and stir overnight. The mixture was concentrated to near dryness, the residue triturated with hexanes, the solids removed by filtration, and the filtrate concentrated and the crude material subjected to flash chromatography using ethyl acetate/hexanes as eluent to give the title compound (12 g) as an oil.

$^1$H NMR 300MHz (CDCl$_3$) 3.50 (1H, m), 3.20 (1H, m), 2.83 (3H, s), 2.30 (3H, s), 1.60–1.90 (2H, m), 1.20–1.60 (14H, m), 0.90 (3H, t).

c) 6-Methyl-2-{3-[1-methylaminohexyl]thio}nicotinonitrile dihydrochloride

To a stirred solution of [3-(acetylthio)-hexyl]methylcarbamic acid, 1,1-dimethylethyl ester (0.70 g, 2.4 mmol) in ethanol (20 ml) at room temperature was added in succession 1N sodium hydroxide solution (6 ml) and 2-chloro-6-methylnicotinonitrile (0.5 g, 3.3 mmol). The mixture was stirred overnight concentrated, and partitioned between ethyl acetate and water. The resulting crude product obtained from the organics was subjected to flash chromatography using ethyl acetate/hexanes as eluent to give the carbamate protected product as an oil. This material was stirred with 4M hydrogen chloride in dioxane (6 ml) for several hours, concentrated to dryness, triturated with isopropanol to give the title compound (160 mg) as a white solid.

MS (APCI+) $^m/z$ 264. (M+1)$^+$.

$^1$H NMR 300 MHz (d$_6$-DMSO) 8.58 (2H, brs), 8.10 (1H, d), 7.20 (1H, d), 4.10 (1H, m), 3.30 (3H, s), 3.00 (1H, br m), 2.50 (3H, s), 2.05 (2H, m), 1.70 (2H, m), 1.45 (2H, m), 0.90 (3H, t).

EXAMPLE 2

6-Trifluoromethyl-2-{3-[1-methylaminohexyl]thio}nicotinonitrile hydrochloride Prepared by the method of Example 1 using [3-(acetylthio)-hexyl]methylcarbamic acid, 1,1-dimethylethyl ester and 2-chloro-6-(trifluoromethyl)nicotinonitrile to give the title compound which was isolated as the hydrochloride salt.

MS (APCI+) $^m/z$ 317 (M+1)$^+$.

$^1$H NMR 300 MHz (d$_6$-DMSO) 8.84 (2H, brs) 8.11 (1H, d), 8.00 (1H, s), 7.80 (1H, d), 3.87 (1H, m), 3.30 (3H, s), 3.05 (1H, br m), 2.55 (3H, s), 2.00 (2H, m), 1.60 (2H, m), 1.45 (2H, m), 0.90 (3H, t).

EXAMPLE 3

2-[1-Ethyl-3-(methylamino)propoxy]-6-(trifluoromethyl)-3-pyridinecarbonitrile hydrochloride a) 1,1-Dimethylethyl N-methyl-(3-oxopropyl)carbamate

Dimethylsulfoxide (6.22 ml, 87.6 mmol) was dissolved in dry dichloromethane (100 ml) under nitrogen and the solution was cooled to −78° C. with stirring. Oxalyl chloride (3.95 ml, 45.4 mmol) was then added dropwise and the solution was stirred at −78° C. for a further 30 minutes when effervescence had ceased. A solution of 1,1-dimethylethyl (3-hydroxypropyl)methylcarbamate (6.62 g, 35.0 mmol) in dichloromethane (100 ml) was then added dropwise at −78° C. The resultant solution was stirred at −78° C. for 45 minutes, then a solution of methylamine (24.4 ml, 175 mmol) in dichloromethane (50 ml) was added. The resultant solution was allowed to warm to room temperature and stirred for a further 18 h. The reaction mixture was then poured into brine and extracted with dichloromethane three times. The combined organic fractions were then washed with brine, dried (MgSO$_4$) and evaporated. The residue was triturated with diethyl ether and filtered. The solvent was evaporated to give the title compound (6.60 g, 100%) as an orange oil.

$^1$H NMR 300 MHz (CDCl$_3$) 9.81 (1H, s), 3.55 (2H, t), 2.87 (3H, s), 2.68 (2H, t), 1.45 (9H, s).

b) 1,1-Dimethylethyl (3-hydroxypentyl)methylcarbamate

N-Methyl-(3-oxopropyl)carbamic acid, 1,1-dimethylethyl ester (2.00 g, 10.7 mmol) was dissolved in tetrahydrofuran (20 ml) under nitrogen and cooled to 0° C. with stirring. To the resulting solution was added ethylmagnesium bromide and the mixture stirred at 0° C. for a further 30 minutes and then allowed to warm to room temperature with stirring over 20 h. The mixture was then poured into saturated ammonium chloride solution and then extracted with diethyl ether three times. The combined organic fractions were then washed with brine and dried over magnesium sulfate. The solvent was evaporated and the residue eluted down a flash chromatography column using 40% diethyl ether/isohexane as eluent to give 1.70 g (65%) of the title compound as an oil.

$^1$H NMR 300 MHz (CDCl$_3$) 3.90 (1H, m), 2.90–3.50 (2H, m), 2.85 (3H, s), 1.70 (2H, m), 1.50 (11H, m), 0.96 (3H, t).

c) 1,1-Dimethylethyl [3-[[3-cyano-6-(trifluoromethyl)-2-pyridinyl]oxy]pentyl]methylcarbamate 2-Chloro-6-(trifluoromethyl)nicotinonitrile (207 mg) and 1,1-dimethylethyl (3-hydroxypentyl)methylcarbamate (217 mg) were dissolved in dimethylformamide (10 ml) under nitrogen at room temperature. To the resulting solution was added sodium hydride (60% in oil) (80 mg). The solution was then allowed to stir at room temperature under nitrogen for 24 h. The mixture was then poured into water and extracted with diethyl ether three times. The combined organic fractions were washed with brine and then dried ($MgSO_4$). The solvent was evaporated and the residue was purified by chromatography (silica, 25% ethyl acetate/isohexane as eluent) to give 175 mg (45%) of the subtitle compound as an oil.
$^1$H NMR 300 MHz ($CDCl_3$) 8.04 (1H, d), 7.31 (1H, d), 5.23 (1H, m), 3.33 (2H, bs), 2.85 (3H, s), 1.77–2.08 (4H, m), 1.40 (9H, s), 0.98 (3H, t).

d) 2-[1-Ethyl-3-(methylamino)propoxy]-6-(trifluoromethyl)-3-pyridinecarbonitrile hydrochloride 1,1-Dimethylethyl [3-[[3-cyano-6-(trifluoromethyl)-2-pyridinyl]oxy]pentyl]methylcarbamate (170 mg) was dissolved in 4M HCl in dioxane (10 ml). The resulting solution was stirred at room temperature for 2 h, then the solvent was evaporated. The residue was recrystallised from diethyl ether/ethanol to give the title compound (100 mg) as a white solid.
MS APCI+ve $^m/z$ 288([M+H]$^+$).
$^1$H NMR 360 MHz ($d_6$-DMSO) 8.69 (2H, bs), 8.61 (1H, d), 7.70 (1H, d), 5.23 (2H, m), 2.99 (2H, m), 2.54 (3H, s), 2.06 (2H, m), 1.76 (2H, m), 0.91 (3H, t).

EXAMPLE 4

2-[[1-Ethyl-3-(methylamino)propyl]thio]-6-methyl-3-pyridinecarbonitrile hydrochloride a) S-[3-[[(1,1-Dimethylethoxy)carbonyl]methylamino]-1-ethylpropyl]benzenecarbothioate To a solution of triphenylphosphine (1.25 g) in tetrahydrofuran (20 ml) under nitrogen at 0° C. was added diisopropylazodicarboxylate (0.95 ml) dropwise. The mixture was stirred at 0° C. for 45 minutes and then a solution of thiobenzoic acid (640 mg) and 1,1-dimethylethyl (3-hydroxypentyl)methylcarbamate (500 mg) in tetrahydrofuran (20 ml) added dropwise at 0° C. After the addition was complete the mixture was stirred at room temperature for 20 h. The mixture was concentrated and the residue was purified by chromatography (silica, 10% diethyl ether/isohexane as eluent) to give the sub-title compound (425 mg) as a yellow oil.
$^1$H NMR 300 MHz ($CDCl_3$) 7.98 (2H, dd), 7.57 (1H, t), 7.44 (2H, t), 3.68 (1H, m), 3.22–3.49 (2H, m), 2.86 (3H, s), 1.66–2.01 (4H, m), 1.45 (9H, s), 1.02 (3H, t).

b) 1,1-Dimethylethyl [3-[(3-cyano-6-methyl-2-pyridinyl)thio]pentyl]methylcarbamate To a mixture of 2-chloro-6-methyl-3-pyridinecarbonitrile (92 mg) and S-[3-[[(1,1-dimethylethoxy)carbonyl]methylamino]-1-ethylpropyl]benzenecarbothioate (200 mg) in methanol (5 ml) was added potassium carbonate (90 mg). The mixture was heated to reflux under nitrogen for 20 h. The mixture was then concentrated, water added and extracted with ethyl acetate three times. The organic layers were combined, washed with brine, dried ($MgSO_4$) and then concentrated. The residue was purified by chromatography (silica, 10% ethyl acetate/isohexane as eluent) to give the sub-title compound (110 mg) as an oil.
$^1$H NMR 300 MHz ($CDCl_3$) 7.65 (1H, d), 6.88 (1H, d), 4.04 (1H, m), 3.37 (2H, t), 2.85 (3H, s), 2.55 (3H, s), 1.69–2.00 (4H, m), 1.44 (9H, s), 1.03 (3H, t).

c) 2-[[1-Ethyl-3-(methylamino)propyl]thio]-6-methyl-3-pyridinecarbonitrile hydrochloride 1,1-Dimethylethyl [3-[(3-cyano-6-methyl-2-pyridinyl)thio]pentyl]methylcarbamate (110 mg) was dissolved in 4M HCl in dioxane (10 ml). The resulting solution was stirred at room temperature for 1 h, then the solvent was evaporated off. The residue was recrystallised from diethyl ether/ethanol to give the title compound (90 mg) as a white solid.
MS APCI+ve $^m/z$ 250 ([M+H]$^+$). $^1$H NMR 300 MHz ($d_6$-DMSO) 8.70 (2H, bs), 8.10 (1H, d), 7.20 (1H, d), 4.01 (1H, m), 3.32 (3H, s), 3.00 (2H, t), 2.54 (3H, s), 2.05 (2H, m), 1.72 (2H, m), 0.99 (3H, t).

EXAMPLE 5

2-[1-Cyclopentyl-3-(methylamino)thiopropyl]-6-(trifluoromethyl)-3-pyridinecarbonitrile Prepared by the method of Example 1 using [3-(acetylthio)-3-(cyclopentyl)propyl]methylcarbamic acid, 1,1-dimethylethyl ester and 2-chloro-6-(trifluoromethyl)nicotinonitrile to give the title compound which was isolated as the oxalate salt.
MS (APCI+) $^m/z$ 344 (M+1)$^+$.
$^1$H NMR 300 MHz ($d_6$-DMSO) 8.54 (1H, d), 7.82 (1H, d), 4.09 (1H, m), 3.05 (2H, m), 2.50 (3H, s), 2.19 (4H, m), 1.80 (1H, d), 1.58 (4H, m), 1.35 (2H, m).

EXAMPLE 6

2-[1-Cyclopentyl-3-(methylamino)thiopropyl]-6-methyl-3-pyridinecarbonitrile

Prepared by the method of Example 1 using [3-(acetylthio)-3-(cyclopentyl)propyl]methylcarbamic acid, 1,1-dimethylethyl ester and 2-chloro-6-(methyl)nicotinonitrile to give the title compound which was isolated as the oxalate salt
MS (APCI+) $^m/z$ 290 (M+1)$^+$.
$^1$H NMR 300 MHz ($d_6$-DMSO) 8.58 (1H, brs), 8.08 (1H, d), 7.19 (1H, d), 4.19 (1H, m), 3.07 (2H, m), 2.59 (3H, s), 2.50 (3H, s), 2.17 (4H, m), 1.85 (1H, d), 1.58 (4H, m), 1.32 (2H, m).

Intermediate 1 tert-Butyl (R)-N-Methyl-N-(4,4,4-trifluoro-3-hydroxybutyl)carbamate a) (R)-4,4,4-Trifluoro-1,3-butanediol

A solution of ethyl (R)-(+)-4,4,4trifluoro-3-hydroxybutyrate (3.12 g, 16.8 mmol) in diethyl ether (8 mL) was added to a 0–5° C. suspension of lithium aluminium hydride (1.01 g, 26.6 mmol) in diethyl ether (17 mL) over 25 minutes. Upon complete addition, the mixture was stirred at ambient temperature for 20 h. The mixture was cooled to 0–5° C. and quenched by dropwise addition of 3N HCl (17 mL), followed by stirring at ambient temperature for 3 h. The liquid portion was decanted away and the salts were washed with additional diethyl ether. The combined organic portions were washed (brine), dried, and evaporated to give the product as a cloudy, colourless oil (2.34 g, 96%).

$^1$H NMR (d$_6$-DMSO) 1.47–1.77 (m, 2H), 3.44–3.61 (m, 2H), 3.92–4.10 (m, 1H), 4.46–4.62 (m, 1H), 6.01 (d, J 6.6 Hz, 1H).

b) (R)-1,1,1-Trifluoro-4-iodo-2-butanol

Triphenylphosphine (5.09 g, 19.4 mmol) was dissolved in dichloromethane (66 mL) and treated with imidazole (1.33 g, 19.5 mmol) and iodine (4.92 g, 19.4 mmol), respectively, to give an orange suspension. A solution of (R)-4,4,4-trifluoro-1,3-butanediol (2.34 g, 16.2 mmol) in dichloromethane (18 mL) was added to the suspension and stirred for 30 minutes. The reaction mixture was placed on a silica gel flash column and eluted with 100% dichloromethane to give the product as a pale purple oil (3.30 g, 80%).

$^1$H NMR (d$_6$-DMSO) 1.89–2.09 (m, 2H), 3.17–3.45 (m, 2H), 3.89–4.06 (m, 1H), 6.38 (d, J 6.6 Hz, 1H).

c) (R)-4Azido-1,1,1-trifluoro-2-butanol

A solution of (R)-1,1,1-trifluoro-4-iodo-2-butanol (3.30 g, 13.0 mmol) in DMSO (22 mL) was treated with sodium azide (0.930 g, 14.3 mmol) at ambient temperature, followed by heating at 50° C. for 20 h. The mixture was diluted with cold water (250 mL) and extracted with diethyl ether. The combined organic extracts were washed (brine), dried, and evaporated without heat to give the product as a pale yellow oil (2.20 g, 100%).

$^1$H NMR (d$_6$-DMSO) 1.60–1.88 (m, 2H), 3.34–3.61 (m, 2H), 3.92–4.08 (m, 1H), 6.32 (d, J 6.6 Hz, 1H).

d) (R)-(4,4,4-Trifluoro-3-hydroxybutyl)carbamic acid tert-butyl ester

A solution of (R)-4-azido-1,1,1-trifluoro-2-butanol (2.20 g, 13.0 mmol) in THF (27 mL) was treated with water (6 mL) and triphenylphosphine (3.41 g, 13.0 mmol) at ambient temperature. After 18 h, di-t-butyldicarbonate (3.56 g, 16.3 mmol) was added and string continued for 3 h. The mixture was concentrated under reduced pressure, and the residue was diluted with water and extracted with diethyl ether. The combined organic extracts were washed (brine), dried, and evaporated to a pale yellow oil. The crude material was purified by silica gel chromatography, eluting with 1:1 hexane/diethyl ether (v/v) and 100% diethyl ether to give the product as a pale yellow oil (3.17 g, 100%).

$^1$H NMR (d$_6$-DMSO) 1.38 (s, 9H), 1.46–1.77 (m, 2H), 2.95–3.15 (m, 2H), 3.85–4.00 (m, 1H), 6.05–6.12 (m, 1H), 6.78–6.87 (m, 1H).

e) (R)-1,1,1-Trifluoro-4-methylamino-2-butanol

A solution of (R)-(4,4,4-trifluoro-3-hydroxybutyl)carbamic acid tert-butyl ester (3.17 g, 13.0 mmol) in THF (130 mL) was treated with lithium aluminium hydride (1.97 g, 52.0 mmol) at ambient temperature, followed by refluxing for 2 h. Heating was stopped, additional lithium aluminium hydride (0.490 g, 12.9 mmol) was added, and refluxing was continued for 1 h. The mixture was cooled to 0–5° C. and carefully quenched with excess sodium sulfate decahydrate. Additional THF and diethyl ether were added to aid stirring. The mixture was filtered through Celite™ and the filtrate was evaporated to a white wax. The wax was purified by trituration with 9:1 hexane/diethyl ether (v/v) to give the product as a white solid (1.56 g, 76%).

$^1$H NMR (d$_6$-DMSO) 1.47–1.74 (m, 2H), 2.20 (s, 3H), 2.56–2.68 (m, 2H), 2.97–3.67 (br m, 2H), 3.96–4.11 (m,1H).

f) tert-Butyl (R)-N-Methyl-N-(4,4,4trifluoro-3-hydroxybutyl)carbamate

A solution of (R)-1,1,1-trifluoro-4-methylamino-2-butanol (1.56 g, 9.93 mmol) in THF (45 mL) was treated with di-t-butyldicarbonate (2.73 g, 12.5 mmol) at ambient temperature. After 4 h, the mixture was concentrated under reduced pressure and the residue was purified by silica gel chromatography, eluting with 1:1 hexane/diethyl ether (v/v) and 100% diethyl ether to give the product as a colourless oil (2.55 g, 100%).

$^1$H NMR (d$_6$-DMSO) 1.39(s, 9H), 1.53–1.86 (m, 2H), 2.78 (s, 3H), 3.23–3.37 (m, 2H), 3.82–3.96 ((m, 1H), 6.16 (d, J 6.6 Hz, 1H).

EXAMPLE 7

(R)-2-(3-Methylamino-1-trifluoromethylpropoxy)-6-trifluoromethyl-nicotinonitrile hydrochloride a) (R)-[3-(3-Cyano-6-trifluoromethyl-pyridin-2-yloxy)-4,4,4-trifluorobutyl]methylcarbamic acid tert-butyl ester A mixture of 2-chloro-6-(trifluoromethyl)nicotinonitrile (0.410 g, 1.98 mmol) and tert-butyl (R)-N-methyl-N-4,4,4-trifluoro-3-hydroxybutyl)carbamate (0.480 g, 1.87 mmol) in DMF (8 mL) was treated with caesium carbonate (1.29 g, 3.96 mmol) at ambient temperature. After stirring for 19 h, the mixture was diluted with water and extracted with diethyl ether. The combined organic extracts were washed (water, brine), dried, and evaporated to a brown oil that was purified by silica gel chromatography, eluting with 100% dichloromethane and 5% methanol/95% dichloromethane (v/v) to give the product as a pale yellow oil (0.793 g, 99%).

$^1$H NMR (d$_6$-DMSO) 1.25 (s, 9H), 2.02–2.28 (m, 2H), 2.76 (s, 3H), 3.20–3.63 (m, 2H), 5.71–5.95 (m, 1H), 7.85 (d, J 7.6 Hz, 1H), 8.71 (d, J 7.7 Hz, 1H).

b) (R)-2-(3-Methylamino-1-trifluoromethylpropoxy)-6-trifluoromethyl-nicotinonitrile hydrochloride A solution of (R)-[3-(3-cyano-6-trifluoromethyl-pyridin-2-yloxy)-4,4,4-trifluorobutyl]methylcarbamic acid tert-butyl ester (0.784 g, 1.83 mmol) in 1,4-dioxane (10 mL) was treated with 4N HCl in 1,4-dioxane (4 mL, 16.0 mmol) and stirred at ambient temperature for 14 h. The mixture was concentrated under reduced pressure and the residue was vacuum dried. The residue was triturated with diethyl ether and collected by vacuum filtration to give the mono-hydrochloride salt of the product as a white solid (0.622 g, 92%).

$^1$H NMR (d$_6$-DMSO) 2.20–2.63 (m, 5H), 3.00–3.40 (m, 2H), 6.00–6.17 (m, 1H), 7.89 (d, J 7.8 Hz, 1H),8.67–8.96 (m, 3H).

MS: $^m$/z 328 (M+1)$^+$.

EXAMPLE 8

(R)-5-Fluoro-6-methyl-2-(3-methylamino-1-trifluoromethylpropoxy)nicotinonitrile hydrochloride a) (R)-[3-(3-Cyano-5-fluoro-6-methylpyridin-2-yloxy)4,4-trifluorobutyl]-methylcarbamic acid tert-butyl ester A mixture of 2-chloro-5-fluoro-6-methylnicotinonitrile (0.144 g, 0.844 mmol) and tert-butyl (R)-N-methyl-N-(4,4,4-trifluoro-3-hydroxybutyl)carbamate (0.196 g, 0.762 mmol) in DMF (4 mL) was treated with caesium carbonate (0.510 g, 1.56 mmol). After stirring at ambient temperature for 21 h, the mixture was diluted with water and extracted with diethyl ether. The combined organic extracts were washed (water, brine), dried, and evaporated to an orange oil which was purified by silica gel chromatography, eluting with 1:1 hexane/diethyl ether (v/v), to give the product as an orange oil (0.079 g, 26%).

$^1$H NMR ($d_6$-DMSO) 1.30 (s, 9H), 1.95–2.24 (m, 2H), 2.40–2.46 (m, 3H), 2.76 (s, 3), 5.76–5.93 (m, 1H), 8.40 (d, J 8.4 Hz, 1H).

MS: $^m$/z 414 (M+23)$^+$.

b) (R)-5-Fluoro-6-methyl-2-(3-methylamino-1-trifluoromethylpropoxy)nicotinonitrile hydrochloride A solution of (R)-[3-(3-cyano-5-fluoro-6-methylpyridin-2-yloxy)-4,4,4-trifluorobutyl]-methylcarbamic acid tert-butyl ester (0.075 g, 0.192 mmol) in 1,4-dioxane (1 mL) was treated with 4N HCl in 1,4-dioxane (0.5 mL, 2.0 mmol) and stirred at ambient temperature for 15 h. Additional 4N HCl in 1,4-dioxane (0.5 mL, 2.0 mmol) was added and stirring continued for 4 h. The mixture was concentrated under reduced pressure and the residue was vacuum dried. The residue was taken up in diethyl ether and collected by vacuum filtration to give the mono-hydrochloride salt of the product as a white solid (0.053 g, 84%).

$^1$H NMR ($d_6$-DMSO) 1.95–2.40 (m, 2H), 2.56 (s, 3H), 2.97–3.12 (m, 2H), 6.00–6.15 (m, 1H), 8.43 (d, J=8.4 Hz, 1H), 8.80–8.95 (br s, 2H).

MS: $^m$/z 292 (M+1)$^+$.

EXAMPLE 9

(R)-6-Ethyl-5-fluoro-2-(3-methylamino-1-trifluoromethylpropoxy)nicotinonitrile hydrochloride a) (R)-[3-(3-Cyano-6-ethyl-5-fluoro-pyridin-2-yloxy-4,4,4-trifluorobutyl]-methylcarbamic acid tert-butyl ester A solution of tert-butyl (R)-N-methyl-N-(4,4,4-trifluoro-3-hydroxybutyl)carbamate (0.203 g, 0.789 mmol) in THF (3 mL) was treated with sodium hydride (60% dispersion in mineral oil, 0.050 g, 1.25 mmol) at ambient temperature, followed by treatment with a solution of 2-chloro-6-ethyl-5-fluoronicotinonitrile (0.147 g, 0.796 mol) in THE (2 mL). After heating at 50° C. for 22 h, the mixture was diluted with water and extracted with diethyl ether. The combined organic extracts were washed (1N NaOH, water, brine), dried, and evaporated to a yellow oil which was purified by silica gel chromatography, eluting with 3:1 hexane/diethyl ether (v/v), to give the product as a colourless oil (0.180 g, 56%).

$^1$H NMR ($d_6$-DMSO) 1.22 (t, J=7.5 Hz, 3H), 1.29 (s, 9H), 1.97–2.26 (m, 2H), 2.68–2.85 (m, 5H), 3.24–3.45 (m, 2H), 5.80–5.96 (m, 1H), 8.40 (d, J 8.6 Hz, 1H).

MS: $^m$/z 406 (M+1)$^+$.

b) (R)-6-Ethyl-5-fluoro-2-(3-methylamino-1-trifluoromethylpropoxy)nicotinonitrile hydrochloride A solution of (R)-[3-(3-cyano-6-ethyl-5-fluoro-pyridin-2-yloxy)-4,4,4-trifluorobutyl]-methylcarbamic acid tert-butyl ester (0.175 g, 0.432 mmol) in 1,4-dioxane (2.3 mL) was treated with 4N HCl in 1,4-dioxane (1.2 mL, 4.8 mmol) and stirred at ambient temperature for 24 h. Additional 4N HCl in 1,4-dioxane (1.0 mL, 4.0 mmol) was added and stirring continued for 2.5 h. The mixture was concentrated under reduced pressure and vacuum dried for 1 h. The residue was triturated with diethyl ether and collected by vacuum filtration to give the mono-hydrochloride salt of the product as a white solid (0.135 g, 91%).

$^1$NMR ($d_6$-DMSO) 1.25 (t, J=7.5 Hz, 3H), 2.15–2.42 (m, 2H), 2.55 (s, 3H), 2.75–2.87 (m, 2H), 2.97–3.13 (m, 2H), 6.02–6.15 (m, 1H), 8.42 (d, J 8.7 Hz, 1H), 8.90 (br s, 2H).

MS: $^m$/z 306 (M+1)$^+$.

EXAMPLE 10

6-Methyl-2-(3-methylamino-1-trifluoromethylpropoxy)nicotinonitrile hydrochloride a) Toluene-4-sulfonic acid 4,4,4-trifluoro-3-hydroxybutyl ester

A 0–5° C. solution of 4,4,4-trifluoro-1,3-butanediol[1] (2.00 g, 13.4 mmol) in pyridine (4.8 mL) was treated with p-toluenesulfonyl chloride (3.18 g, 16.7 mmol). The mixture was stirred cold for 4 h, followed by stirring at ambient temperature for 19 h. The mixture was poured into ice containing 2N HCl (20 mL). The aqueous material was extracted with dichloromethane. The combined organic extracts were washed (2N HCl, water, brine), dried, and evaporated to a brown oil. The oil was purified by silica gel chromatography, eluting with 100% dichloromethane and 5% methanol/95% dichloromethane (v/v), to give the product as an amber oil (1.30 g, 32%).

[1] Janzen, E. G.; Zhang, Y. K.; Arimura, M., *J. Org. Chem.* 1995, 60, :5434–5440

$^1$H NMR ($d_6$-DMSO) 1.67–1.98 (m, 2H), 2.43 (s, 3H), 3.90–4.24 (m, 3H), 6.33 (d, J 6.6 Hz, 1H), 7.49 (d, J 8.1 Hz, 1H), 7.80 (d, J 8.1 Hz, 1H).

b) 4-Azido-1,1,1-trifluoro-2-butanol

A solution of 4-toluenesulfonic acid 4,4,4-trifluoro-3-hydroxybutyl ester (1.30 g, 4.36 mmol) in DMSO (7 mL) was treated with sodium azide (0.306 g, 4.71 mmol) at is ambient temperature and then heated at 50° C. for 23 h. The mixture was diluted with cold water and extracted with diethyl ether. The combined organic extracts were washed (brine), dried, and evaporated without heat to give the product as a yellow oil (0.737 g, 100%).

$^1$H NMR ($d_6$-DMSO) 1.60–1.90 (m, 2H), 3.26–3.63 (m, 2H), 3.94–4.10 (m, 1H), 6.32 (d, J=6.7 Hz, 1H).

c) (4,4,4-Trifluoro-3-hydroxybutyl)carbamic acid tert-butyl ester

A solution of 4-azido-1,1,1-trifluoro-2-butanol (0.737 g, 4.36 mmol) in THF (9 mL) was treated with water (2 mL)

and triphenylphosphine (1.15 g, 4.38 mmol) at ambient temperature. After stirring for 16 h, di-t-butyldicarbonate (1.11 g, 5.08 mmol) was added and stirring continued for 4 h. The mixture was concentrated under reduced pressure, diluted with water, and extracted with diethyl ether. The combined organic extracts were washed (brine), dried, and evaporated to a tan oil. The crude oil was purified by silica gel chromatography, eluting with 1:1 hexane/diethyl ether (v/v), to give the product as an oil (1.06 g, 100%).

$^1$H NMR (d$_6$-DMSO) 1.38 (s, 9H), 1.45–1.80 (m, 2H), 2.96–3.18 (m, 2H), 3.87–4.03 (m, 1H), 6.07–6.13 (m, 1H), 6.78–6.88 (m, 1H).

d) 1,1,1-Trifluoro-4-methylamino-2-butanol

A solution of (4,4,4-trifluoro-3-hydroxybutyl)carbamic acid tert-butyl ester (0.55 g, 2.26 mmol) in THF (21 mL) was treated with lithium aluminium hydride (0.321 g, 8.46 mmol) at ambient temperature, followed by refluxing for 3 h. The mixture was cooled to ambient temperature and carefully quenched with excess sodium sulphalte decahydrate. Additional THF and diethyl ether were added to aid stirring. The mixture was filtered through a bed of Celite™ and the filtrate was evaporated to a white solid. The solid was purified by silica gel chromatography, eluting with 10% 2M ammonia in methanol/90% dichloromethane and 20% 2M ammonia in methanol/80% dichloromethane (v/v), to give the product as a white solid (0.218 g, 61%).

$^1$H NMR (d$_6$-DMSO) 1.48–1.76 (m, 2H), 2.28 (s, 3H), 2.53–2.70 (m, 2H), 3.00–3.66 (br m, 2H), 3.94–4.13 (m, 1H).

e) tert-Butyl N-methyl-N-(4,4,4-trifluoro-3-hydroxybutyl)carbamate

A solution of 1,1,1-trifluoro-4-methylamino-2-butanol (0.211 g, 1.34 mmol) in THF (6 mL) was treated with di-t-butyldicarbonate (0.367 g, 1.68 mmol) and stirred at ambient temperature for 4 h. The mixture was concentrated under reduced pressure and the residue was purified by silica gel chromatography, eluting with 1:1 hexane/diethyl ether (v/v) to provide the product as a yellow oil (0.345 g, 100%).

$^1$H NMR (d$_6$-DMSO) 1.39 (s, 9H), 1.50–1.88 (m, 2H), 2.78 (s, 3H), 3.80–3.98 (m, 1H), 6.13–6.20 (m, 1H).

f) [3-(3-Cyano-6-methyl-pyridin-2-yloxy)-4,4,4-trifluorobutyl]-methylcarbamic acid tert-butyl ester A mixture of 2-chloro-6-methylnicotinonitrile (0.215 g, 1.41 mmol) and tert-butyl N-methyl-N-(4,4,4-trifluoro-3-hydroxybutyl)carbamate (0.345 g, 1.34 mmol) in DMF (6 mL) was treated with caesium carbonate (0.875 g, 2.69 mmol) at ambient temperature. After stirring for 4 days, the mixture was diluted with water and extracted with diethyl ether. The combined organic extracts were washed (water, brine), dried, and evaporated to an orange oil/solid mixture. The crude material was purified by silica gel chromatography, eluting with 100% dichloromethane and 5% methanol/95% dichloromethane (v/v) to give the product as a yellow oil (0.156 g, 31%).

$^1$H NMR (d$_6$-DMSO) 1.29 (s, 9H), 1.95–2.25 (m, 2H), 2.43–2.54 (m, 3H), 2.76 (s, 3H), 5.87–6.03 (m, 1H), 7.18 (d, J 7.8 Hz, 1H), 8.23 (d, J 7.5 Hz, 1H).

MS: $m/z$ 274 (M−100)$^+$.

g) 6-Methyl-2-(3-methylamino-1-trifluoromethylpropoxy)nicotinonitrile hydrochloride A solution of [3-(3-cyano-6-methyl-pyridin-2-yloxy)-4,4,4-trifluorobutyl]-methylcarbamic acid tert-butyl ester (0.150 g, 0.402 mmol) in 1,4-dioxane (3 mL) was treated with 4N HCl in 1,4-dioxane (1.0 mL, 4.0 mmol) at ambient temperature and stirred for 17 h. The mixture was concentrated and the residue was vacuum dried. The residue was triturated with diethyl ether and collected by vacuum filtration to give the mono-hydrochloride salt of the product as a white solid (0.100 g, 90%).

$^1$H NMR (d$_6$-DMSO) 2.16–2.70 (m, 5H), 2.94–3.14 (m, 2H), 3.18–4.42 (m, 3H), 6.07–6.24 (m, 1H), 7.22 (d, J 7.7 Hz, 1H), 8.26 (d, J 7.8 Hz, 1H), 8.93 (br s, 2H).

MS: $m/z$ 274 (M+1)$^+$.

EXAMPLE 11

2-(3-Amino-1-trifluoromethylpropoxy)-6-trifluoromethylnicotinonitrile hydrochloride a) 1,1,1-Trifluoro-4-iodo-2-butanol

A solution of triphenylphosphine (1.09 g, 4.16 mmol) in dichloromethane (14 mL) was treated with imidazole (0.283 g, 4.16 mmol) and iodine (1.06 g, 4.16 mmol), respectively, to give an orange suspension. A solution of 4,4,4-trifluoro-1,3-butanediol (0.500 g, 3.47 mmol) in dichloromethane (4 mL) was added to the suspension and stirred for 20 minutes. The solid was removed by filtration and the filtrate was concentrated under reduced pressure without heat to yield a black oil. The crude oil was purified by silica gel chromatography, eluting with 100% dichloromethane, to give the product as an oil (0.640 g, 72%).

$^1$H NMR (d$_6$-DMSO) 1.87–2.10 (m, 2H), 3.17–3.47 (m, 2H), 3.88–4.07 (m, 1H), 6.39 (d, J 6.3 Hz, 1H).

b) 4-Azido-1,1,1-trifluoro-2-butanol

A solution of 1,1,1-trifluoro-4-iodo-2-butanol (0.604 g, 2.38 mmol) in DMSO (4 mL) was treated with sodium azide (0.178 g, 2.74 mmol) at ambient temperature, followed by heating at 50° C. for 21 h. The mixture was diluted with cold water and extracted with ethyl acetate. The combined organic extracts were washed (brine), dried, and evaporated to give the product as a pale yellow oil (0.372 g, 92%).

$^1$H NMR (d$_6$-DMSO) 1.60–1.89 (m, 2H), 3.37–3.63 (m, 2H), 3.93–4.11 (m, 1H), 6.31 (d, J 6.6 Hz, 1H).

c) 2-(3-Azido-1-trifluoromethylpropoxy)-6-trifluoromethylnicotinonitrile

A mixture of 2-chloro-6-(trifluoromethyl)nicotinonitrile (0.675 g, 3.27 mmol) and 4-azido-1,1,1-trifluoro-2-butanol (0.552 g, 3.26 mmol) in DMF (8.5 mL) was treated with caesium carbonate (2.18 g, 6.69 mmol) at ambient temperature. After 20 h, the mixture was diluted with water and extracted with diethyl ether. The combined organic extracts were washed (water, brine), dried, and evaporated to give the product as a brown oil (1.01 g, 90%).

$^1$H NMR (d$_6$-DMSO) 2.07–2.30 (m, 2H), 3.46–3.66 (m, 2H), 5.98–6.13 (m, 1H), 7.87 (d, J 7.8 Hz, 1H), 8.72 (d, J 7.5 Hz, 1H).

d) [3-(3-Cyano-6-trifluoromethylpyridin-2-yloxy)-4,4,4-trifluorobutyl]carbamic acid tert-butyl ester A solution of 2-(3-azido-1-trifluoromethylpropoxy)-6-trifluoromethylnicotinonitrile (1.00 g, 2.95 mmol) in THF (6 mL) was treated with water (1.3 mL) and triphenylphosphine (0.774 g, 2.95 mmol) at ambient temperature and was stirred for 18 h. Di-t-butyldicarbonate (0.710 g, 3.25 mmol) was added. After 3 h, the mixture was concentrated under reduced pressure. The residue was diluted with water and extracted with diethyl ether. The combined organic extracts were washed (water, brine), dried, and evaporated to a brown oil. The crude material was purified by silica gel chromatography, eluting with 100% dichloromethane and 5% methanol/95% dichloromethane (v/v) to give the product as a solid (0.212 g, 17%).

$^1$H NMR ($d_6$-DMSO) 1.25 (s, 9H), 2.00–2.13 (m, 2H), 3.00–3.36 (m, 2H), 5.85–5.96 (m, 1H), 6.78–6.87 (m, 1H), 7.84 (d, J 7.8 Hz, 1H), 8.70 (d, J 7.5 Hz, 1H).

e) 2-(3-Amino-1-trifluoromethylpropoxy)-6-trifluoromethylnicotinonitrile hydrochloride A solution of [3-(3-cyano-6-trifluoromethylpyridin-2-yloxy)-4,4,4-trifluorobutyl]carbamic acid tert-butyl ester (0.212 g, 0.513 mmol) in 1,4-dioxane (3 mL) was treated with 4N HCl in 1,4-dioxane (0.5 mL, 2.0 mmol) at ambient temperature and stirred for 24 h. Additional 4N HCl in 1,4-dioxane (0.5 mL, 2.0 mmol) was added and stirring continued for 6 h. The mixture was concentrated under reduced pressure and vacuum dried for 30 minutes. The residue was triturated with diethyl ether and collected by vacuum filtration to give the mono-hydrochloride salt of the product as a white solid (0.081 g, 45%).

$^1$H NMR ($d_6$-DMSO) 2.11–2.47 (m, 2H), 2.86–3.14 (m, 2H), 6.00–6.18 (m, 1H), 7.80–8.25 (m, 4H), 8.65–8.78 (m, 1H).

MS: $m/z$ 314 (M+1)$^+$.

EXAMPLE 12

5-Fluoro-6-ethyl-2-{3-[1-methylaminopentyl]thio}nicotinonitrile dihydrochloride a) 2-Chloro-5-fluoro-6-ethyl-3-pyridinecarbonitrile

To a vigorously stirred mixture of 2,6-dichloro-5-fluoro-3-pyridinecarbonitrile (15.0 g, 78.5 mmol), potassium phosphate (17.0 g, 74.0 mmol), and [1,1'-bis(diphenylphosphino)ferrocene]dichloropalladium(II) (1.5 g, 1.8 mmol) in dry THF (300 ml) at room temperature was added in a stream triethylborane (85 ml of a 1M solution in THF). The resulting mixture was heated at reflux temperature for 16 h, cooled, concentrated, and partitioned between ethyl acetate and water. The resulting crude product obtained from the organics was subjected to flash chromatography using ethyl acetate/hexanes as eluent to give the title compound (8 g) as a solid.

$^1$H NMR 300 MHz (CDCl$_3$) 7.62 (1H, d), 2.90 (2H, m), 1.30 (3H, t).

b) 5-Fluoro-6-ethyl-2-{3-[1-methylaminopentyl]thio}nicotinonitrile dihydrochloride Prepared by the method of Example 1(c) using [3-(acetylthio)-pentyl]methylcarbamic acid, 1,1-dimethylethyl ester and 2-chloro-5-fluoro-6-ethyl-3-pyridinecarbonitrile to give the title compound which was isolated as the hydrochloride salt.

$^1$H NMR 300 MHz (D$_2$O) 7.75 (1H, d), 3.90 (1H, m), 3.21 (2H, t), 2.85 (2H, m), 2.71 (3H, s), 2.17 (1H, m), 2.09 (1H, m), 1.74 (2H, m), 1.25 (3H, t), 0.98 (3H, t).

MS (APCI+) $m/z$ 282 (M+1)$^+$.

EXAMPLE 13

6-Trifluoromethyl-2-{3-[1-methylaminopentyl]thio}nicotinonitrile hydrochloride Prepared by the method of Example 1 but using ethylmagnesium chloride in place of n-propylmagnesium chloride and 2-chloro-6-(trifluoromethyl)nicotinonitrile in place of 2-chloro-6-(methyl)nicotinonitrile to give the title compound which was isolated as the hydrochloride salt.

MS (APCI+) $m/z$ 304 (M+1)$^+$.

$^1$H NMR 300 MHz (D$_2$O) 8.14 (1H, d), 7.55 (1H, d), 3.98 (1H, m), 3.08 (2H, m), 2.57 (3H, s), 2.04 (2H, m), 1.69 (2H, m), 0.90 (3H, t).

EXAMPLE 14

6-Methyl-2-{3-[1-methylaminohex-5-enyl]thio}nicotinonitrile oxalate

Prepared by the method of Example 1 but using 1-propenylmagnesium chloride in place of ethylmagnesium chloride to give the title compound which was isolated as the oxalate salt.

MS (APCI+) $m/z$ 262 (M+1)$^+$.

$^1$H NMR 300 MHz ($d_6$-DMSO) 8.06 (1H, d), 7.19 (1H, d), 5.86 (1H, m), 5.15 (2H, m), 4.16 (1H, m), 3.07 (2H, m), 2.50 (3H, s), 2.50 (2H, m), 2.07 (2H, m).

EXAMPLE 15

2-[1-(2-Aminoethyl)-2,2,3,3,3-pentafluoropropoxy]-6-trifluoromethyl-nicotinonitrile fumarate a) 1,1,1,2,2-Pentafluoro-5-iodo-3-pentanol

To a solution of triphenylphosphine (2.38 g, 9.08 mmol) in dichloromethane (30 ml) was added imidazole (630 mg, 9.25 mmol) followed by iodine (2.30 g, 9.08 mmol). A dark brown suspension was obtained. To this was added a solution of 4,4,5,5,5-pentafluoropentan-1,3-diol[1] (1.47 g, 7.57 mmol) in dichloromethane (8 ml) and diethyl ether (3 ml). Additional dichloromethane (5 ml) and diethyl ether (1 ml) were used to ensure complete transfer. The reaction was complete after 15 minutes. The suspension was filtered to remove a white solid and the filtrate was evaporated to yield a dark brown liquid. Purification by silica gel chromatography using dichloromethane yielded the title compound as a dark brown liquid (1.99 g, 99%).

[1] Kitazume, T.; Ohnogi, T.; Lin, J. T.; Yamazaki, T.; Ito, K. *J. Fluorine Chem.* 1989, 42, 17–29.

$^1$H NMR 300 MHz (CDCl$_3$) 4.28 (m, 1H), 3.28–3.49 (m, 2H), 2.06–2.23 (m, 3H).

b) 5-Azido-1,1,1,2,2-pentafluoro-3-pentanol

A solution of 1,1,1,2,2-pentafluoro-5-iodo-3-pentanol (1.99 g, 7.48 mmol) in dimethylsulfoxide (20 ml) was treated with sodium azide (585 mg, 8.98 mmol) and the reaction was heated to 50° C. After stirring overnight, the reaction was cooled to room temperature. It was then added to water (30 ml) and extracted with diethyl ether (3×30 ml). The combined organics were washed with brine (40 ml) and dried over anhydrous sodium sulphate. Removal of the solvents yielded an orange liquid. Purification by silica gel chromatography using 1:1 hexanes/ethyl acetate gave the title compound as an orange liquid (1.7 g, 100%).

$^1$H NMR 300 MHz (CDCl$_3$) 4.26 (m, 1H), 3.60 (dd, 2H), 3.30 (d, 1H), 1.82–2.05 (m, 2H).

c) 2-[1-(2-Azidoethyl)-2,2,3,3,3-pentafluoropropoxy]-6-trifluoromethyl-nicotinonitrile To a solution of 5-azido-1,1,1,2,2-pentafluoro-3-pentanol (500 mg, 2.28 mmol) in dimethylformamide (10 ml) was added 2-chloro-6-(trifluoromethyl)nicotinonitrile (565 mg, 2.74 mmol) followed by caesium carbonate (2.20 g, 6.75 mmol). The reaction mixture turned brown. After 2 h, the reaction mixture was added to water (10 ml) and extracted with diethyl ether (2×15 ml). The combined organics were washed with brine (20 ml) and dried over anhydrous sodium sulfate. Removal of the solvents yielded a brown liquid. Purification by silica gel chromatography using hexanes/ethyl acetate (10:1 then 1:1) gave the title compound as a yellow liquid (780 mg, 88%).

$^1$H NMR 300 MHz (CDCl$_3$) 8.18 (d, 1H), 7.51 (d, 1H), 6.19 (m, 1H), 3.39–3.62 (m, 2H), 2.25 (m, 2H).

d) 2-[1-(2-Aminoethyl)-2,2,3,3,3-pentafluoropropoxy]-6-trifluoromethyl-nicotinonitrile fumarate To a solution of 2-[1-(2-azidoethyl)-2,2,3,3,3-pentafluoropropoxy]-6-trifluoromethyl-nicotinonitrile (350 mg, 0.899 mmol) in tetrahydrofuran (3.5 ml) and water (3 drops) was added triphenylphosphine (360 mg, 1.35 mmol). After 3 h, the solvents were removed and the residue was loaded directly onto a silica gel column and eluted with dichloromethane followed by 10:1 dichloromethane/2M ammonia in methanol. A yellow liquid (63 mg) was obtained. This was taken up in diethyl ether (3 ml) and added to a stirring solution of fumaric acid (22 mg) in diethyl ether (5 ml) containing a few drops of methanol. The resulting suspension was stirred for 30 minutes and the solid was collected by vacuum filtration and dried overnight under vacuum at 40° C. The title compound was obtained as a white solid (46 mg).

$^1$H NMR 300 MHz (d$_6$-DMSO) 8.75 (d, 1H), 7.89 (d, 1H), 6.55 (s, 2H), 6.24 (m, 1H), 2.99 (m,2H), 2.29 (m, 2H).

MS: $^m$/z 364 (M+1)$^+$.

EXAMPLE 16

2-[1-(2-Aminoethyl)-2,2,3,3,3-pentafluoropropoxy]-6-methyl-nicotinonitrile fumarate The title compound was prepared by the method of Example 15 but using 5-azido-1,1,1,2,2-pentafluoro-3-pentanol and 2-chloro-6-methyl-3-pyridinecarbonitrile to give the title compound which was isolated as the fumarate salt as a white solid in 37% yield.

$^1$H NMR 300 MHz (d$_6$-DMSO) 8.25 (d, 1H), 7.21 (d, 1H), 6.44 (s, 2H), 6.29 (m, 1H), 2.85 (m, 2H), 2.50 (s, 3H), 2.14 (m, 2H).

MS: $^m$/z 310 (M+1)$^+$.

SCREENS

The pharmacological activity of compounds according to the invention may be assessed using the following screens.

Screen 1

The activity of compounds of formula (I), or a pharmaceutically acceptable salt thereof may be screened for nitric oxide synthase inhibiting activity by a procedure based on that of Förstermann et al., Eur. J. Pharm., 1992, 225, 161–165. Nitric oxide synthase converts $^3$H-L-arginine into $^3$H-L-citrulline which can be separated by cation exchange chromatography and quantified by liquid scintillation counting.

Enzyme is prepared, after induction, from the cultured murine macrophage cell line J774A-1 (obtained from the laboratories of the Imperial Cancer Research Fund). J774A-1 cells are cultured in Dulbeccos Modified Eagles Medium (DMEM) supplemented with 10% foetal bovine serum, 4 mM L-glutamine and antibiotics (100 units/ml penicillin G, 100 mg/ml streptomycin & 0.25 mg/ml amphotericin B). Cells are routinely grown in 225 cm$^3$ flasks containing 35 ml medium kept at 37° C. and in a humidified atmosphere containing 5% CO$_2$.

Nitric oxide synthase is produced by cells in response to interferon-g (IFNg) and lipopolysaccharide (LPS). The medium from confluent culture flasks is removed and replaced with 25 ml (per flask) of fresh medium containing 1 mg/ml LPS and 10 units/ml IFNg. After a period of 17–20 hours in culture, harvesting of cells is accomplished by scraping the cell sheet from the flask surface into the culture medium. Cells are collected by centrifugation (1000 g for 10 minutes) and lysate prepared by adding to the cell pellet a solution containing 50 mM Tris-HCl (pH 7.5 at 20° C.), 10% (v/v) glycerol, 0.1% (v/v) Triton-X-100, 0.1 mM dithiothreitol and a cocktail of protease inhibitors comprising leupeptin (2 mg/ml), soya bean trypsin inhibitor (10 mg/ml), aprotinin (5 mg/ml) and phenylmethylsulphonyl fluoride (50 mg/ml).

For the assay, 25 μl of substrate cocktail (50 mM Tris-HCl (pH 7.5 at 20° C.), 400 μM NADPH, 20 μM flavin adenine dinucleotide, 20 μM flavin mononucleotide, 4 μM tetrahydrobiopterin, 12 μM L-arginine and 0.025 mCi L-[$^3$H] arginine) is added to wells of a is 96 well filter plate (0.45 μM pore size) containing 25 μl of a solution of test compound in 50 mM Tris-HCl. The reaction is started by adding 50 μl of cell lysate (prepared as above) and after incubation for 1 hour at room temperature is terminated by addition of 50 μl of an aqueous solution of 3 mM nitroarginine and 21 mM EDTA.

Labelled L-citrulline is separated from labelled L-arginine using Dowex AG-50W. 150 μl of a 25% aqueous slurry of Dowex 50W (Na$^+$ form) is added to the assay after which the whole is filtered into 96 well plates. 75 μl of filtrate is sampled and added to wells of 96 well plates containing solid scintillant After allowing the samples to dry the L-citrline is quantified by scintillation counting.

In a typical experiment basal activity is 300 dpm per 75 μl sample which is increased to 1900 dpm in the reagent controls. Compound activity is expressed as IC$_{50}$ (the concentration of drug substance which gives 50% enzyme inhibition in the assay) and aminoguanidine, which gives an IC$_{50}$ (50% inhibitory concentration) of 10 μM, is tested as a standard to verify the procedure. Compounds are tested at a range of concentrations and from the inhibitions obtained IC$_{50}$ values are calculated. Compounds that inhibit the enzyme by at least 25% at 100 μM are classed as being active and are subjected to at least one retest.

Screen 2

Recombinant human NO synthases (iNOS, eNOS & nNOS) were expressed in E. coli and lysates were prepared in Hepes buffer (pH 7.4) containing co-factors (FAD, FMN, $H_4B$), protease inhibitors, lysozyme and the detergent, CHAPS. These preparations were used, at suitable dilution, to assess inhibition of the various isoforms. Inhibition of NOS was determined by measuring the formation of L-[$^3$H] citrulline from L-[$^3$H]arginine using an adaptation of the method of Förstermann et al.[9] Enzyme assays were performed in the presence of 3 µM [$^3$H]arginine, 1 mM NADPH and other co-factors required to support NOS activity (FAD, FMN, $H_4B$, calmodulin, $Ca^{2+}$). Since various NOS inhibitors have been reported to exhibit slow binding kinetics, or to inactivate the enzyme in a time dependent manner, enzyme and inhibitor were pre-incubated for 60 min in the presence of NADPH before addition of arginine to initiate the reaction. Incubations continued for a further 60 min before the assays were quenched and [$^3$H]citrulline separated from unreacted substrate by chromatography on Dowex-50W resin in a 96-well format.

In the above screen, the compounds of Examples 1 to 16 were tested and gave $IC_{50}$ values of less than 10 µM against the iNOS and nNOS enzymes, and showed good selectivity with respect to the inhibition of eNOS, indicating that they are expected to show useful therapeutic activity.

Screen 3

Compounds also show activity against the human form of induced nitric oxide synthase as can be demonstrated in the following assay.

The human colorectal carcinoma cell line, DLD-1 (obtained from the European Collection of Animal Cell Culture—cell line number 90102540) was routinely grown in RPMI 1640 supplemented with 10%(v/v) foetal bovine serum, and 2 mM L-glutamine, at 37° C. in 5% $CO_2$.

Nitric oxide synthase was induced in cells by addition of medium containing human recombinant gamma-IFN (1000 units/ml), TNF-alpha (200 U/ml), IL-6 (200 U/ml) and IL-1-beta (250 U/ml). After incubation for 18 hours at 37° C., the medium was removed and the cells washed with warm phosphate buffered saline. Cells were incubated for a further 5 hours at 37° C./5% $CO_2$ in RPMI 1640 containing 100µM L-arginine and 100 µM verapamil-HCl in the presence and absence of test compounds.

Nitrite accumulation was determined by mixing an equal volume of culture media with Griess reagent (10 mg/ml sulphanilamide, 1 mg N-(1-naphthyl)ethylenediamine in 1 ml 2.5% (v/v) phosphoric acid). Inhibition in the presence of compounds was calculated relative to the nitrite levels produced by untreated cells. $IC_{50}$ values were estimated from a semi-log plot of % inhibition versus concentration of compound.

The invention claimed is:

1. A compound of formula (I)

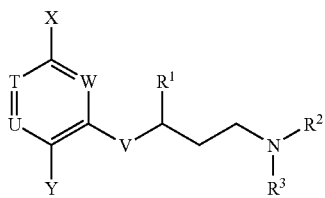

(I)

or a racemate, stereoisomer, or tautomer thereof, wherein:

X is selected from the group consisting of H, C1 to C4 alkyl, C1 to C4 alkoxy, halogen, OH, CN, C≡CH, $NO_2$, CHO, COCH3 and NHCHO, wherein the alkyl or alkoxy group is unsubstituted or optionally substituted by one or more fluorine atoms or by an OH group;

Y is selected from the group consisting of C1 to C4 alkyl, C1 to C4 alkoxy, halogen, OH, CN, C≡CH, $NO_2$, CHO, $COCH_3$ and NHCHO, wherein the alkyl or alkoxy group is unsubstituted or optionally substituted by one or more fluorine atoms;

one of T, U and W is N and the other two are independently $CR^4$, wherein each $R^4$ group is independently selected from the group consisting of H, F, and $CH_3$;

V is O or $S(O)_n$;

n is an integer 0, 1 or 2;

$R^1$ is selected from the group consisting of C1 to C4 alkyl, C2 to C4 alkenyl, C2 to C4 alkynyl, C3 to C6 cycloalkyl, and a 4 to 8 membered saturated heterocyclic ring incorporating one heteroatom selected from O, S and N, wherein any of the said $R^1$ groups is unsubstituted or optionally substituted by a substituent selected from the group consisting of C1 to C4 alkyl, C1 to C4 alkoxy, C1 to C4 alkylthio, C3 to C6 cycloalkyl, one or more halogens, and phenyl, wherein the phenyl group is unsubstituted or optionally substituted by one or more substituents selected independently from the group consisting of halogen, C1 to C4 alkyl, C1 to C4 alkoxy, $CF_3$, $OCF_3$, CN and $NO_2$;

$R^2$ and $R^3$ are independently selected from the group consisting of H, C1 to C4 alkyl and C3 to C6 cycloalkyl, wherein the alkyl group is unsubstituted or optionally substituted by a substituent selected from the group consisting of C1 to C4 alkoxy, halogen, hydroxy, -Z-$NR^7R^8$, phenyl, and a five or six membered aromatic or saturated heterocyclic ring containing 1 to 3 heteroatoms independently selected from O, S and N, wherein the phenyl or aromatic heterocyclic ring is unsubstituted or optionally substituted by one or more groups selected from halogen, C1 to C4 alkyl, C1 to C4 alkoxy, $CF_3$, $OCF_3$, CN, and $NO_2$;

Z is —CO— or a bond; and $R^7$ and $R^8$ are independently H or C1 to C4 alkyl, wherein the compound, racemate, stereoisomer, or tautomer thereof may exist in the form of a pharmaceutically acceptable salt thereof.

2. The compound according to claim 1, wherein V is O.

3. The compound according to claim 1, wherein V is $S(O)_n$ and n is 0.

4. The compound according to claim 1, wherein X is $CH_3$, $CH_3CH_2$ or $CF_3$.

5. The compound according to claim 4, wherein Y is CN.

6. The compound according to claim 1, selected from the group consisting of:

6-methyl-2-{3-[1-methylaminohexyl]thio}nicotinonitrile;

6-trifluoromethyl-2-{3-[1-methylaminohexyl]thio}nicotinonitrile;

2-[1-ethyl-3-(methylamino)propoxy]-6-(trifluoromethyl)-3-pyridinecarbonitrile;

2-[[1-ethyl-3-(methylamino)propyl]thio]-6-methyl-3-pyridinecarbonitrile;

2-[1-cyclopentyl-3-(methylamino)thiopropyl]-6-(trifluoromethyl)-3-pyridinecarbonitrile;

2-[1-cyclopentyl-3-(methylamino)thiopropyl]-6-methyl-3-pyridinecarbonitrile;

(R)-2-(3-methylamino-1-trifluoromethylpropoxy)-6-trifluoromethyl-nicotinonitrile;

(R)-5-fluoro-6-methyl-2-(3-methylamino-1-trifluoromethylpropoxy)nicotinonitrile;
(R)-6-ethyl-5-fluoro-2-(3-methylamino-1-trifluoromethylpropoxy)nicotinonitrile;
6-methyl-2-(3-methylamino-1-trifluoromethylpropoxy)nicotinonitrile;
2-(3-amino-1-trifluoromethylpropoxy)-6-trifluoromethylnicotinonitrile;
5-fluoro-6-ethyl-2-{3-[1-methylaminopentyl]thio}nicotinonitrile;
6-trifluoromethyl-2-{3-[1-methylaminopentyl]thio}nicotinonitrile;
6-methyl-2-{3-[1-methylaminohex-5-enyl]thio}nicotinonitrile;
2-[1-(2-aminoethyl)-2,2,3,3,3-pentafluoropropoxy]-6-trifluoromethyl-nicotinonitrile; and
2-[1-(2-aminoethyl)-2,2,3,3,3-pentafluoropropoxy]-6-methyl-nicotinonitrile;
or a pharmaceutically acceptable salt of the compound.

7. A pharmaceutical formulation comprising a compound according to any one of claims 1 to 6, or a pharmaceutically acceptable salt thereof, in admixture with a pharmaceutically acceptable adjuvant, diluent, or carrier.

8. A process for the preparation of the compound according to any one of claims 1 to 6, wherein the process comprises a step selected from the group consisting of:

(a) reacting a compound of formula (II)

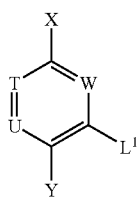

(II)

wherein T, U, X, Y and W are as defined in claim 1 and $L^1$ represents a leaving group, with a compound of formula (III)

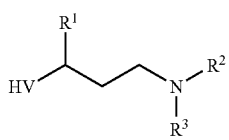

(III)

wherein $R^1$, $R^2$, $R^3$ and V are as defined in claim 1;

(b) reacting a compound of formula (IV)

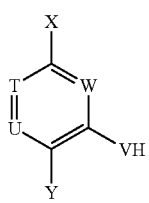

(IV)

wherein T, U, W, X, Y and V are as defined in claim 1, with a compound of formula (V)

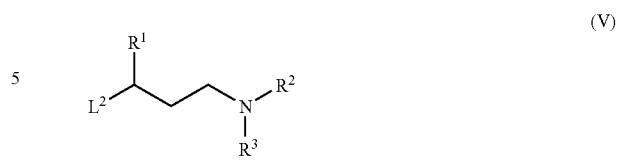

(V)

wherein $R^1$, $R^2$ and $R^3$ are as defined in claim 1 and $L^2$ is a leaving group;

(c) reacting a compound of formula (VI)

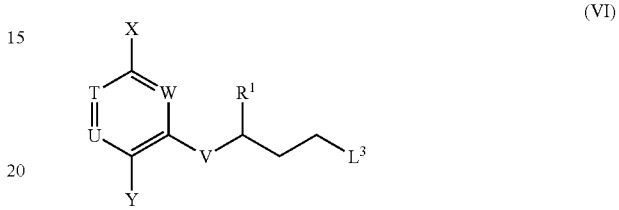

(VI)

wherein $R^1$, T, U, W, X, Y and V are as defined in claim 1 and $L^3$ is a leaving group, with a compound of formula (VII)

$R^2R^3NH$ (VII)

wherein $R^2$ and $R^3$ are as defined in claim 1;

(d) reducing a compound of formula (VIII)

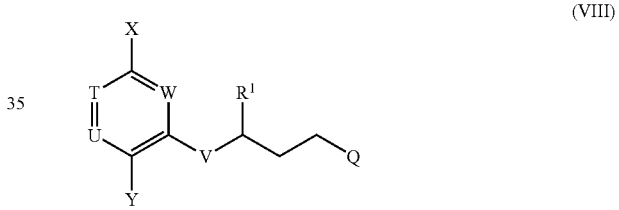

(VIII)

wherein $R^1$, T, U, W, X, Y and V are as defined in claim 1 and Q is azide ($N_3$); and (e) hydrolyzing a compound of formula (VIII)

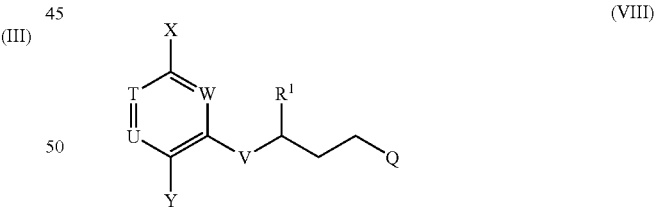

(VIII)

wherein $R^1$, T, U, W, X, Y and V are as defined in claim 1 and Q is an imide group;

wherein each of (a)–(e) may optionally further comprise one or more steps selected from: converting the resultant compound of formula (I), or another salt thereof, into a pharmaceutically acceptable salt thereof; converting one compound of formula (I) into another compound of formula (I); and converting the resultant compound of formula (I) into an optical isomer thereof.

9. A method for the treatment of ischemia, the method comprising administering to a patient in need thereof a therapeutically effective amount of a compound according to any one of claims 1 to 6.

10. A method for the treatment of vasospasm, the method comprising administering to a patient in need thereof a therapeutically effective amount of a compound according to any one of claims 1 to 6.

11. A method for the treatment of inflammation, the method comprising administering to a patient in need thereof a therapeutically effective amount of a compound according to any one of claims 1 to 6.

12. A method for the treatment of an inflammatory disorder selected from the group consisting of rheumatoid arthritis, osteoarthritis, cranial trauma, and migraine, the method comprising administering to a patient in need thereof a therapeutically effective amount of a compound according to any one of claims 1 to 6.

13. The method according to claim 12, wherein the inflammatory disorder is rheumatoid arthritis or osteoarthritis.

14. The method according to claim 12, wherein the inflammatory disorder is migraine.

15. A composition comprising a mixture of tautomers of the compound according to claim 1.

* * * * *

UNITED STATES PATENT AND TRADEMARK OFFICE
CERTIFICATE OF CORRECTION

PATENT NO. : 7,119,109 B2 Page 1 of 1
APPLICATION NO. : 10/484960
DATED : October 10, 2006
INVENTOR(S) : Chen et al.

It is certified that error appears in the above-identified patent and that said Letters Patent is hereby corrected as shown below:

Col. 26
Line 2: "C=CH" should read --C≡CH--.
Line 3: "COCH3" should read --COCH$_3$--.
Line 7: "C=CH" should read --C≡CH--..
Line 42: "arc" should read --are--.

Col. 29
Line 11: "migrainc" should read --migraine--.

Signed and Sealed this

Second Day of January, 2007

JON W. DUDAS
*Director of the United States Patent and Trademark Office*